(12) United States Patent
Hezkiahu et al.

(10) Patent No.: US 11,103,643 B2
(45) Date of Patent: Aug. 31, 2021

(54) BI-DIRECTIONAL ROTATION RESISTANT FRICTION PAD

(71) Applicant: West Pharma. Services IL, Ltd., Ra'anana (IL)

(72) Inventors: Ran Hezkiahu, Herzliya (IL); Samuel Dauphinais, Scottsdale, AZ (US); Jason W. Farris, Gilbert, AZ (US)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/982,202

(22) PCT Filed: Mar. 22, 2019

(86) PCT No.: PCT/US2019/023646
§ 371 (c)(1),
(2) Date: Sep. 18, 2020

(87) PCT Pub. No.: WO2019/183515
PCT Pub. Date: Sep. 26, 2019

(65) Prior Publication Data
US 2021/0030968 A1 Feb. 4, 2021

Related U.S. Application Data

(60) Provisional application No. 62/646,536, filed on Mar. 22, 2018.

(51) Int. Cl.
*A61M 5/00* (2006.01)
*A61M 5/315* (2006.01)
*A61M 5/20* (2006.01)

(52) U.S. Cl.
CPC .......... *A61M 5/31501* (2013.01); *A61M 5/20* (2013.01); *A61M 5/31511* (2013.01);
(Continued)

(58) Field of Classification Search
CPC ............... A61M 5/20; A61M 5/31501; A61M 2005/2086; A61M 2005/3143;
(Continued)

(56) References Cited

U.S. PATENT DOCUMENTS 9,656,019 B2   5/2017  Cabiri et al.
10,086,145 B2  10/2018 Cabiri et al.
(Continued)

FOREIGN PATENT DOCUMENTS

EP    2593162 A1     5/2013
WO    2012007246 A1  1/2012

OTHER PUBLICATIONS

Int'l Preliminary Report on Patentability dated Jun. 25, 2020 in Int'l Application No. PCT/US2019/023646.
(Continued)

*Primary Examiner* — Rebecca E Eisenberg
(74) *Attorney, Agent, or Firm* — Panitch Schwarze Belisario & Nadel LLP

(57) ABSTRACT

An assembly for advancing a piston through a rotationally fixed cartridge includes a rotatable, axially fixed first member and an axially movable, rotatable second member connected thereto via a threaded connection and connectable to the piston. A friction pad is rotationally fixedly connected with the second member and includes first and second sets of fingers extending radially outwardly from a central disk. Both the first and second sets of fingers are configured to contact an interior side wall of the cartridge. The first set of fingers are angled toward a first rotational direction and are configured to wedge the friction pad between the side wall and the second member upon rotation of the first member in the first direction, thereby substantially preventing rotation in the first direction. The second set of fingers are angled toward a second rotational direction and are configured to substantially prevent rotation in the second direction.

10 Claims, 7 Drawing Sheets

(52) U.S. Cl.
CPC .................. *A61M 5/31585* (2013.01); *A61M 2005/2086* (2013.01); *A61M 2005/3151* (2013.01); *A61M 2005/31508* (2013.01)

(58) Field of Classification Search
CPC ........... A61M 2005/31508; A61M 2005/3151; A61M 2005/3152; A61M 5/31; A61M 5/31511; A61M 5/31585; F16D 65/567
See application file for complete search history.

(56) References Cited

U.S. PATENT DOCUMENTS

| | | | |
|---|---|---|---|
| 2013/0245596 A1* | 9/2013 | Cabiri | A61M 5/14248 604/500 |
| 2013/0267895 A1* | 10/2013 | Hemmingsen | A61M 5/31511 604/93.01 |
| 2013/0296799 A1* | 11/2013 | Degtiar | A61M 5/1452 604/220 |
| 2016/0296711 A1* | 10/2016 | Blancke | A61M 5/3146 |
| 2017/0080158 A1 | 3/2017 | Cabiri et al. | |
| 2017/0143907 A1* | 5/2017 | Stever | A61M 5/20 |
| 2017/0175859 A1* | 6/2017 | Brockmeier | A61M 5/31511 |
| 2017/0224924 A1* | 8/2017 | Christensen | A61M 5/3155 |

OTHER PUBLICATIONS

Int'l Search Report and Written Opinion dated Jul. 22, 2019 in PCT Application No. PCT/US2019/023646.

* cited by examiner

BI-DIRECTIONAL ROTATION RESISTANT FRICTION PAD

CROSS REFERENCE TO RELATED APPLICATIONS

This application is a Section 371 of International Application No. PCT/US2019/023646, filed Mar. 22, 2019, which was published Sep. 26, 2019 under International Publication No. WO 2019/183515 A1, and claims priority from U.S. Provisional Patent Application No. 62/646,536, titled "Bi-Directional Rotation Resistant Friction Pad", filed on Mar. 22, 2018, the entire contents of each of which are incorporated by reference herein.

BACKGROUND OF THE DISCLOSURE

The present disclosure is generally directed to an anti-rotational friction fitting, and more particularly, to a friction fitting for preventing rotation of a piston in a reservoir of an injector, and enabling axial advancement of a driving assembly of an injector.

Conventional automatic injectors typically include a container, e.g., a cartridge, containing a substance therein, rotationally stabilized within the injector housing. The container is generally sealed at a rear end by an axially advanceable piston. A driving assembly is utilized to drive the piston through the container to dispense the substance from the container, e.g., via an injection needle. Telescopic driving assemblies are often employed in automatic injectors, which are configured to translate rotational motion, originating, for example, from a motor coupled therewith, into axial/linear motion. Such telescopic driving assembly generally include an axially fixed, rotatable first shaft and a threadedly connected, rotatable and axially movable second shaft. To translate rotation of the first shaft into axial advancement of the second shaft, an anti-rotation mechanism is required to prevent rotation of the second shaft.

Friction fittings may be employed to interface between the second shaft and the rotationally fixed container, to prevent rotation of the second shaft as a result of the frictional force therebetween. One drawback of friction fittings is that they are generally configured to oppose rotation in one direction. Accordingly, the friction fitting must be manufactured to prevent the direction of rotation outputted by the driving assembly, and, thereafter, ensured to be assembled in the proper orientation relative to the driving assembly in order to achieve the desired rotational resistance.

Accordingly, it would beneficial to manufacture generic and universal, bi-directional friction fittings capable of providing sufficient rotational resistance in either the clockwise or counter-clockwise directions, thereby eliminating a required assembly orientation of the friction fittings relative to the driving assemblies. Such a fitting would reduce manufacturing and/or assembly errors, as well as reduce the measures required to be taken to avoid such errors.

BRIEF SUMMARY OF THE DISCLOSURE

Briefly stated, one aspect of the present disclosure is directed to an assembly for advancing a piston through a rotationally fixed cartridge, the cartridge having a front end, an open rear end and a substance filled therein between the piston and the front end. The assembly includes an axially fixed first member rotatable in either a first rotational direction or an opposing second rotational direction and an axially movable, rotatable second member connected to the first member via a threaded connection and connectable to the piston. A friction pad is rotationally fixedly connected with a distal end of the second member and includes a central disk, a first set of fingers extending radially outwardly from the central disk and a second set of fingers extending radially outwardly from the central disk. Both the first set and the second set of fingers are configured to contact an interior side wall of the cartridge. The first set of fingers are angled toward the first rotational direction and are configured to wedge the friction pad between the interior side wall and the second member upon rotation of the first member in the first rotational direction, thereby substantially preventing rotation of the friction pad and the second member in the first rotational direction relative to the cartridge. The second set of fingers are angled toward the second rotational direction and are configured to wedge the friction pad between the interior side wall and the second member upon rotation of the first member in the second rotational direction, thereby substantially preventing rotation of the friction pad and the second member in the second rotational direction relative to the cartridge.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Figure 1:
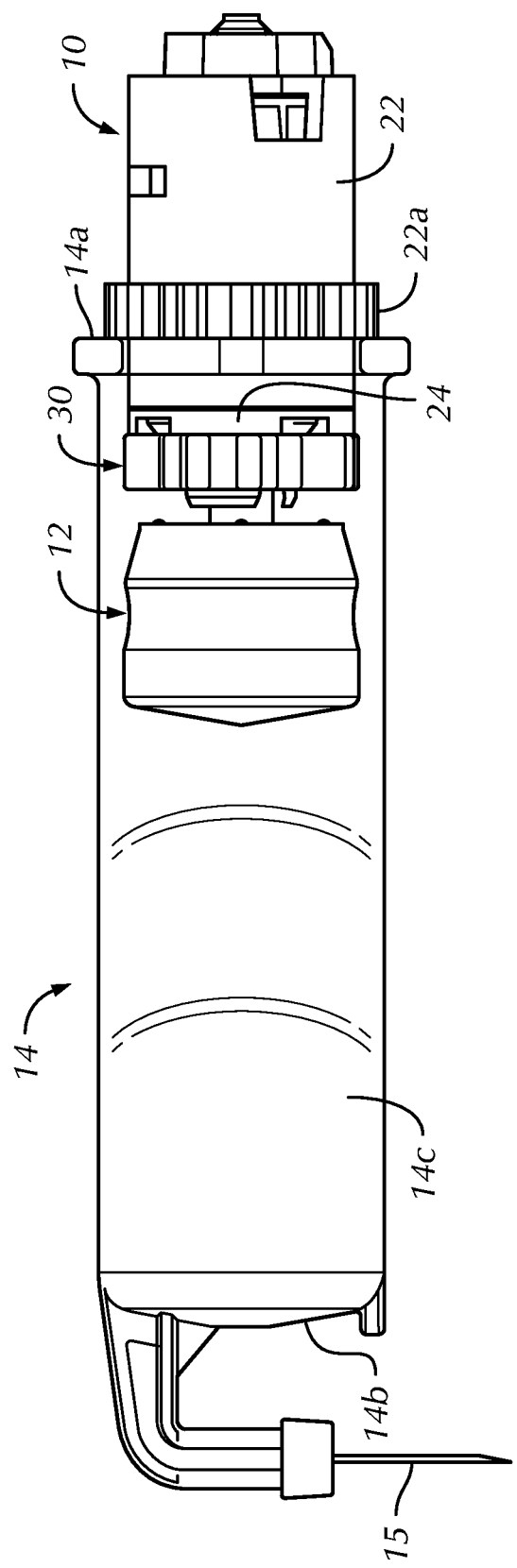
FIG. 1 is side elevational view of an assembled driving assembly, piston and container, employing a bi-directional friction pad between the driving assembly and the piston, in accordance with an embodiment of the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of an injector, and designated parts thereof, such as, for example, a cartridge, a driving assembly, or a friction pad, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-7B a driving assembly 10 for advancing a piston 12 through a rotationally fixed drug container 14, e.g., a cartridge, a syringe or the like, in accordance with an embodiment of the present disclosure. In one configuration, the driving assembly 10, the piston 12 and the cartridge 14 may be inserted, assembled, or otherwise coupled to an injector (not shown), such as, for example, a wearable automatic injector, but the disclosure is not so limited. When the cartridge 14 is coupled to the injector housing (not shown), the cartridge 14 is rotationally fixed and optionally immobilized with respect to the housing via any of numerous mechanisms well understood by those of ordinary skill in the art.

Figure 2:
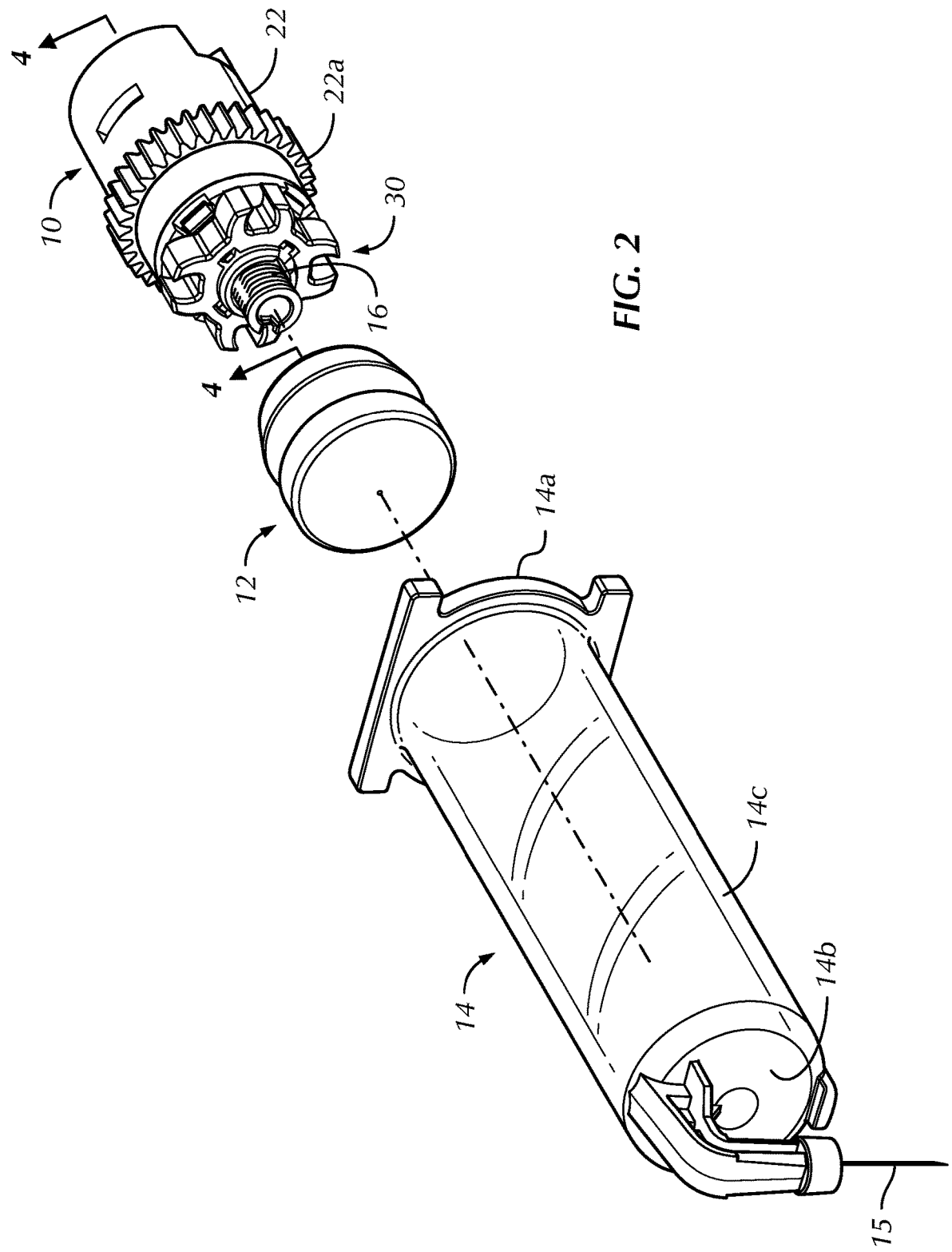
FIG. 2 is an exploded view of the driving assembly, piston, friction pad and container of FIG. 1.
Figure 3:
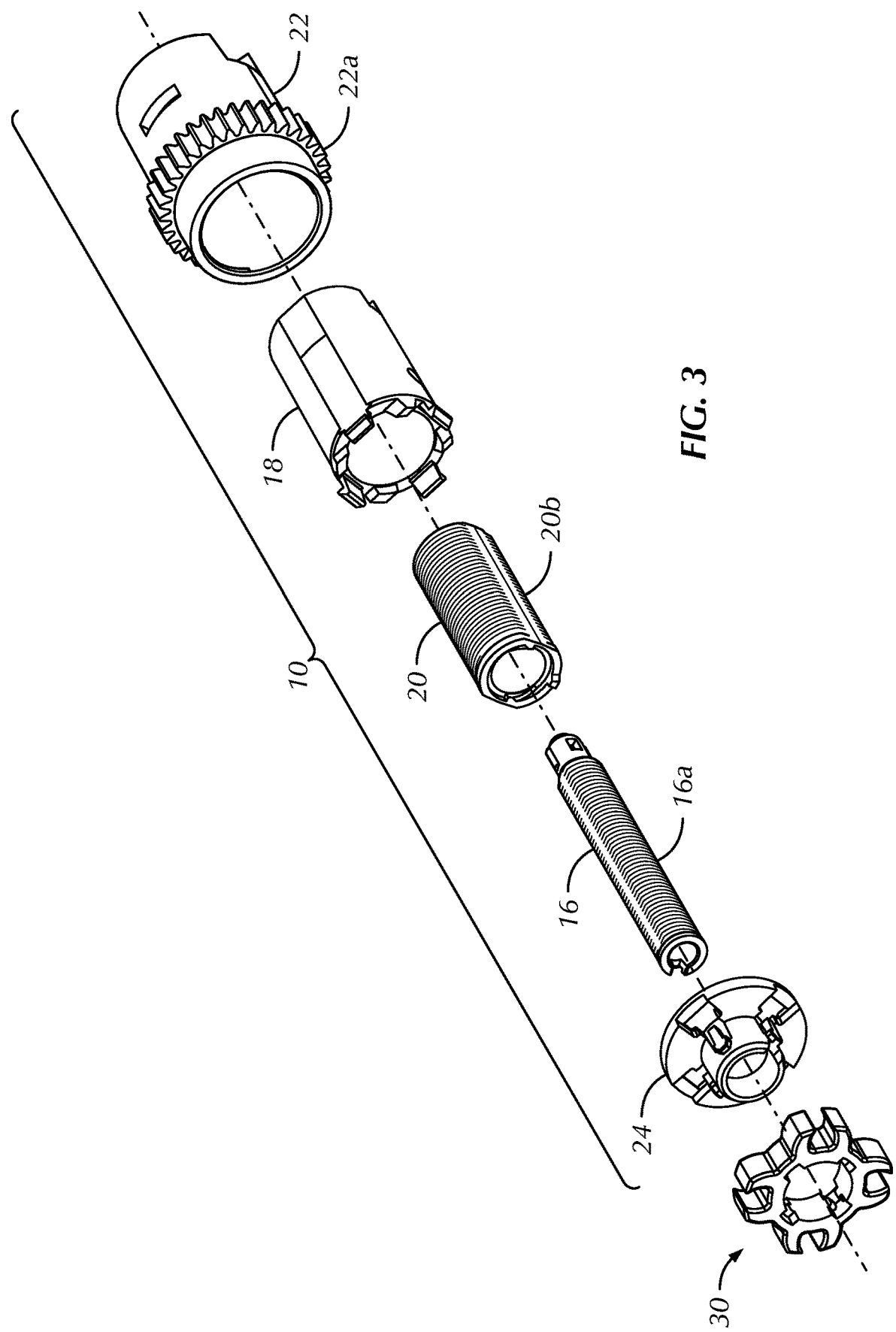
FIG. 3 is an exploded view of the driving assembly and friction pad of FIG. 1.
Figure 4:
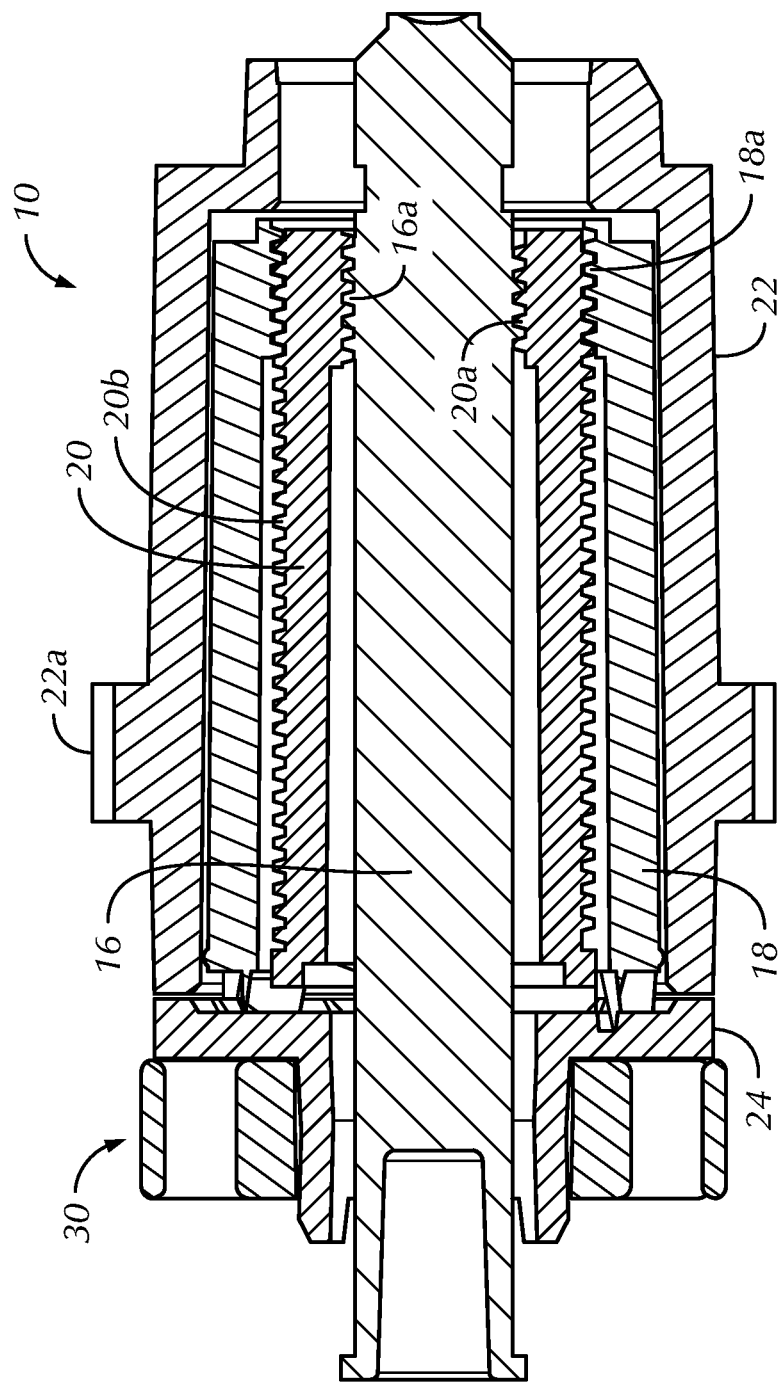
FIG. 4 is a cross-sectional view of the driving assembly in a contracted configuration thereof and the friction pad of FIG. 1, taken along the sectional line 4-4 of FIG. 2.

As should be understood, the container 14 includes an open proximal/rear end 14a, a distal/front end 14b and a reservoir 14c extending therebetween. In the illustrated embodiment, the cartridge 14 includes an injection needle 15 extending from the distal end 14b thereof. As should be understood by those of ordinary skill in the art, however, the cartridge 14 may alternatively include a penetrable septum (not shown) at the distal end thereof, configured for penetration by an opposing needle (not shown). The piston 12 is sized and dimensioned in a manner well understood by those of ordinary skill in the art for sealed engagement with the interior sidewall of the reservoir 14c, via the open proximal end 14a of the cartridge 14, and axial advancement through the reservoir 14c, e.g., for dispensing a substance filled in the reservoir 14c between the piston 12 and the distal end 14b, through the injection needle 15. In FIGS. 1 and 2, the cartridge 14 is shown being transparent/translucent for viewing the open rear end 14a and the piston 12, but the disclosure is not so limited.

The piston 12 is engageable at a proximal end thereof by the driving assembly 10 for advancement of the piston 12 through the reservoir 14c. In one non-limiting example, the driving assembly 10 may take the form of a telescoping driving assembly as described in U.S. Pat. No. 9,656,019, entitled "Apparatuses For Securing Components Of A Drug Delivery System During Transport And Method Of Using Same", the entire contents of which are incorporated by reference herein. As shown in an exemplary, non-limiting configuration in FIGS. 1-4, the driving assembly 10 may include a first member 16 in the form of a first shaft, a second member 18 in the form of a second shaft, an optional third member 20 in the form of a third shaft, an optional cartridge gear 22, and an optional pushing element/cover 24. As shown best in FIG. 4, the first shaft 16 is axially fixed to, and rotatable with, the cartridge gear 22 in a manner well understood by those of ordinary skill in the art. For example, the rear end of the first shaft 16 may be snap fitted, and in keyed engagement, with the rear end of the cartridge gear 22. Therefore, the first shaft 16 is rotatable in a first rotatable direction, e.g., clockwise, or a second rotatable direction, e.g., counter-clockwise, depending upon the rotational direction of the cartridge gear 22. The cartridge gear 22 includes an external gear 22a configured for engagement with an actuator (not shown), e.g., a motor, for rotation of the cartridge gear 22. Alternatively, the first shaft 16 may be axially fixed to the injector housing itself (not shown), and rotatable relative thereto and in direct connection with the actuator (not shown).

At least two of the components of the driving assembly 10 are threaded and/or nested together, whereby axial/linear motion is achieved by a rotating/screwing motion between the threaded components. In the illustrated configuration of FIGS. 3 and 4, the first shaft 16 defines external threading 16a and the second shaft 18 defines internal threading 18a (see FIG. 4). In the illustrated configuration, the third shaft 20 is interposed between the first shaft 16 and the second shaft 18, but the disclosure is not so limited. The third shaft 20 defines internal threading 20a engaged with the external threading 16a of the first shaft 16, and the third shaft 20 also defines external threading 20b engaged with the internal threading 18a of the second shaft 18. The threaded engagement between the first shaft 16 and the third shaft 20 permits rotation and axial motion of the third shaft 20 relative to the first shaft 16. Similarly, the threaded engagement between the third shaft 20 and the second shaft 18 permits rotation and axial motion of the second shaft 18 relative to the first and third shafts 16, 20.

In a contracted configuration of the driving assembly 10 (FIGS. 1, 4), the first, second and third shafts 16, 18, 20 are nested within the cartridge gear 22. In an expanded configuration (not shown), achieved by rotation of the first shaft 16, the third shaft 20 is telescopically extended relative to the first shaft 16 and the second shaft 18 is telescopically extended relative to the third shaft 20. Alternatively, the second shaft 18 may be directly threadedly engaged with the first shaft 16 (without a third shaft 20 therebetween), and rotatable and axially movable relative thereto. A pushing cover 24, polymeric or the like, is optionally engaged with a distal end of the second shaft 18, e.g., via a plurality of snap fittings.

In an alternative, exemplary, non-limiting configuration (not shown) of the driving assembly 10, the first member 16 may take the form of an axially fixed screw, rotatable with the cartridge gear 22 or directly engaged with the actuator (not shown), and the second member 18 may take the form of an axially movable, rotatable nut in threaded engagement with the screw. Conversely, in yet another alternative, exemplary, non-limiting configuration (not shown) of the driving assembly 10, the first member 16 may take the form of an axially fixed nut, rotatable with the cartridge gear 22 or directly engaged with the actuator (not shown), and the second member 18 may take the form of an axially movable, rotatable screw in threaded engagement with the nut.

A friction pad 30, constructed from a flexible material, such as, for example, a polymer, elastomer, silicone, combinations thereof, or the like, is rotationally fixedly connected with the distal end of the second shaft 18, e.g., via the pushing cover 24, to provide rotational resistance to the second shaft 18 (as will be described in further detail below), thereby enabling axial/linear extension of the second shaft 18 upon rotation of the axially fixed first shaft 16, to expand the driving assembly 10. The friction pad 30 may be injection molded or compression molded, depending on construction material, or made via other methods currently known or that later become known in the art. Alternatively, the friction pad 30 and the pushing cover 24 may be formed as a single over-molded component. The pushing cover 24 operates as a friction pad adapter, connecting the friction pad 30 with the second shaft 18. Alternatively, the distal end of the second shaft 18 may be configured to directly connect with the friction pad 30.

The friction pad 30 includes a central disk 32, with a first set of fingers 34 extending radially outwardly therefrom and a second set of fingers 36 also extending radially outwardly therefrom. The central disk 32 includes an inner periphery 32a defining a central aperture 32b. In one embodiment, the inner periphery 32a may include a plurality of angularly spaced slots/grooves 33. The pushing cover 24 may include a generally planar surface 24a and a projection 26 extending distally from the surface 24a. The projection 26 of the pushing cover 24 is configured to generally mate with the central aperture 32b of the friction pad 30 and the surface 24a abuts an underside of the friction pad 30 (see FIGS. 1, 4).

Figure 5:
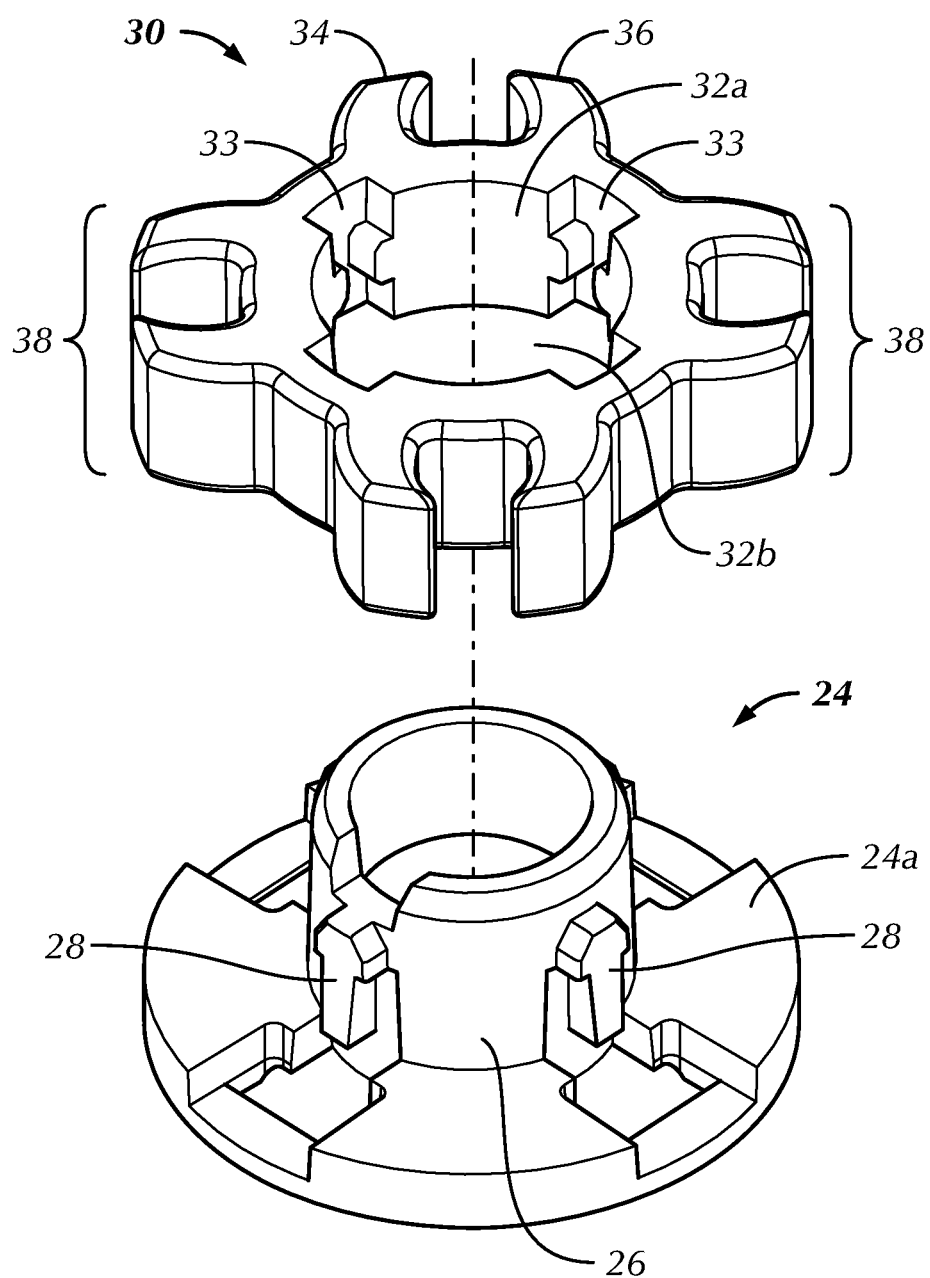
FIG. 5 is an enlarged, perspective exploded view of the friction pad of FIG. 1 and a friction pad adapter for connecting the friction pad with the driving assembly.
Figure 6:
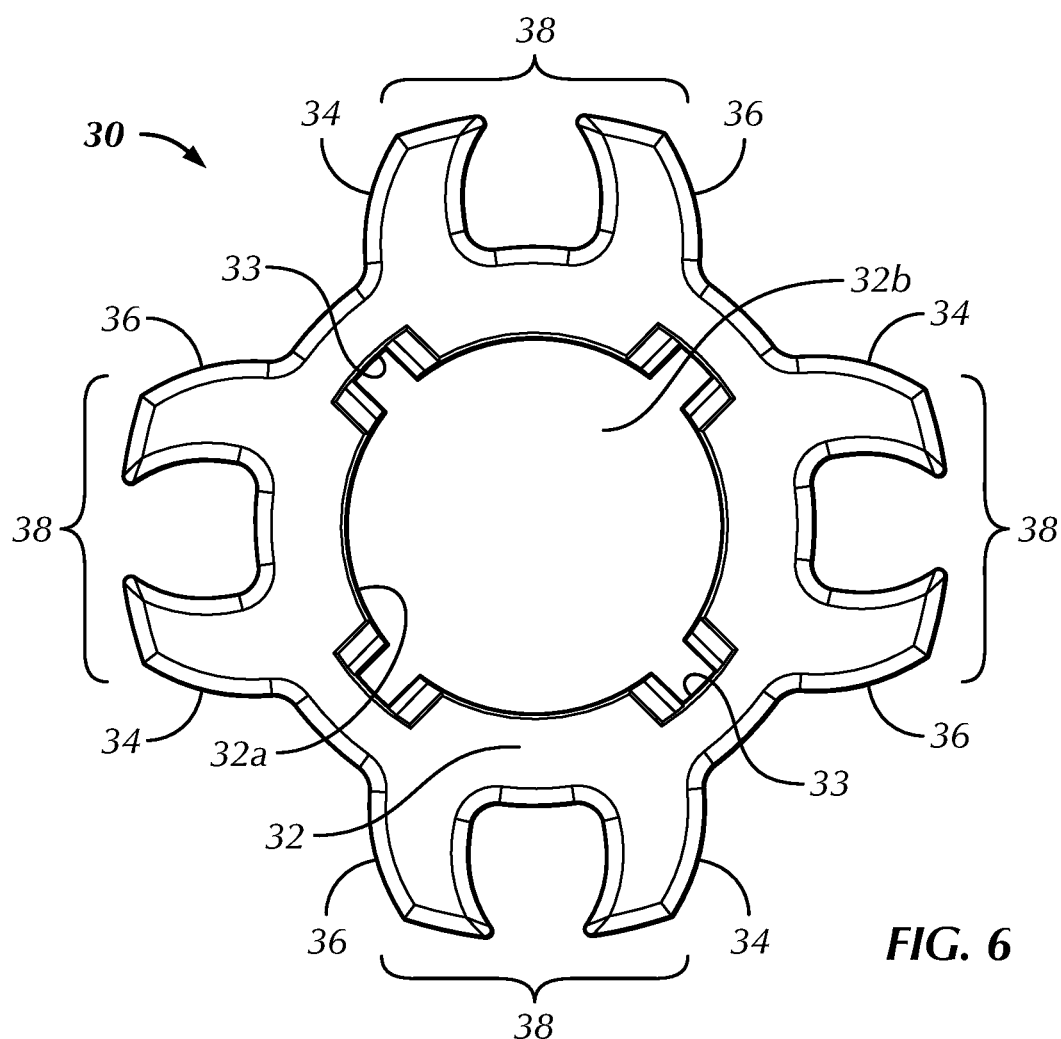
FIG. 6 is an enlarged, top plan view of the friction pad of FIG. 1.

The projection 26 also includes a plurality of tabs 28 corresponding to the slots 33 and configured to engage/mate therewith. Engagement of the tabs 28 of the pushing cover 24 with the corresponding slots 33 of the friction pad 30 rotationally fixes the friction pad 30 relative to the pushing cover 24. In one embodiment, as shown in FIG. 5, the slots 33 may define respective constricted/narrowed portions and the tabs 28 may define respective widened portions, creating a snap fit between the respective tabs 28 and corresponding slots 33 upon advancement of the widened portions beyond the narrowed portions. Advantageously, as shown best in FIG. 5, the narrowed portions of the respective slots 33 are positioned at a midpoint of the slots 33, such that the friction pad 30 may be equally mountable onto the pushing cover 24 in a forward or backward orientation. Further advantageously, the abutment of the surface 24a of the pushing cover 24 with the underside of the friction pad 30 in combination with the snap fit engagement between the respective tabs 28 and the corresponding slots 33 serves to also axially fix the friction pad 30 with the pushing cover 24 in both the forward and backward axial directions. Accordingly, upon assembly of the friction pad 30 with the pushing cover 24, the friction pad 30 remains engaged with the pushing cover 24 in response to forward axial movement through the cartridge reservoir 14c, e.g., via the driving assembly 10, as well as in response to withdrawal of the driving assembly 10 and the friction pad 30 from the cartridge reservoir 14c (if required). Alternatively, the friction pad 30 may be rotationally and axially fixedly connected to the pushing cover 24, or directly to the second shaft 18, via other attachments mechanisms currently known or that later become known, such as, for example, as described in U.S. Pat. No. 10,086,145, entitled "Rotation Resistant Friction Adapter For Plunger Driver Of Drug Delivery Device", the entire contents of which are incorporated by reference herein.

Turning to the fingers, both the first and second sets of fingers 34, 36 are configured to contact the interior side wall of the cartridge 14 when positioned therein to engage the piston 12. The first and second set of fingers 34, 36 are configured, i.e., sized and dimensioned, to engage the interior side wall of the cartridge reservoir 14c via an interference/friction fit, i.e., the external dimension of the friction pad 30, e.g., the diameter about the fingers 34, 36, slightly exceeds the internal dimension/diameter of the cartridge reservoir 14c. Accordingly, the fingers 34, 36 each apply a radially outwardly directed force onto the sidewall of the cartridge reservoir 14c, i.e., a normal force onto the sidewall of the cartridge reservoir 14c.

The fingers 34, 36 of the respective first and second sets of fingers 34, 36 are positioned (relative to the other fingers 34, 36 of the respective first and second set of fingers 34, 36) such that the forces applied on the cartridge reservoir 14c substantially offset one another (in magnitude and direction) in order to maintain the friction pad 30 generally centralized within the cartridge reservoir 14c and aligned with the second shaft 16 without exerting a shear force upon the second shaft 18. In the illustrated embodiment, the first set of fingers 34 includes four fingers substantially equally angularly spaced about the periphery of the central disk 32, and the second set of fingers 36 also includes four fingers substantially equally angularly spaced about the periphery of the central disk 32, but the disclosure is not so limited (with respect to spacing and/or to number of fingers). In the illustrated embodiment, each finger 34 of the first set of fingers is also positioned opposing a finger 36 of the second set of fingers thereby forming a respective pair of fingers 38, wherein the fingers 34, 36 of each respective pair of fingers 38 are positioned mirroring one another, but the disclosure is also not so limited. As one non-limiting example, each of the first and second sets of fingers 34, 36 may include more or less than four fingers. For example, each of the first and second sets of fingers 34, 36, may include two, three or more than four fingers, respectively. The fingers of each set of fingers 34, 36 may, for example, be divided into diametrically opposed groups.

Each finger 34 of the first set of fingers 34 is angled toward the first rotational direction, i.e., clockwise, and each finger 36 of the second set of fingers 36 is angled toward the second rotational direction, i.e., counter-clockwise. In the illustrated embodiment, as shown best in FIG. 6, the fingers 34, 36 of both the first and second set of fingers are arcuate. That is, the fingers 34 are curved toward the first rotational direction and the fingers 36 are curved toward the second rotational direction.

Figure 7A:
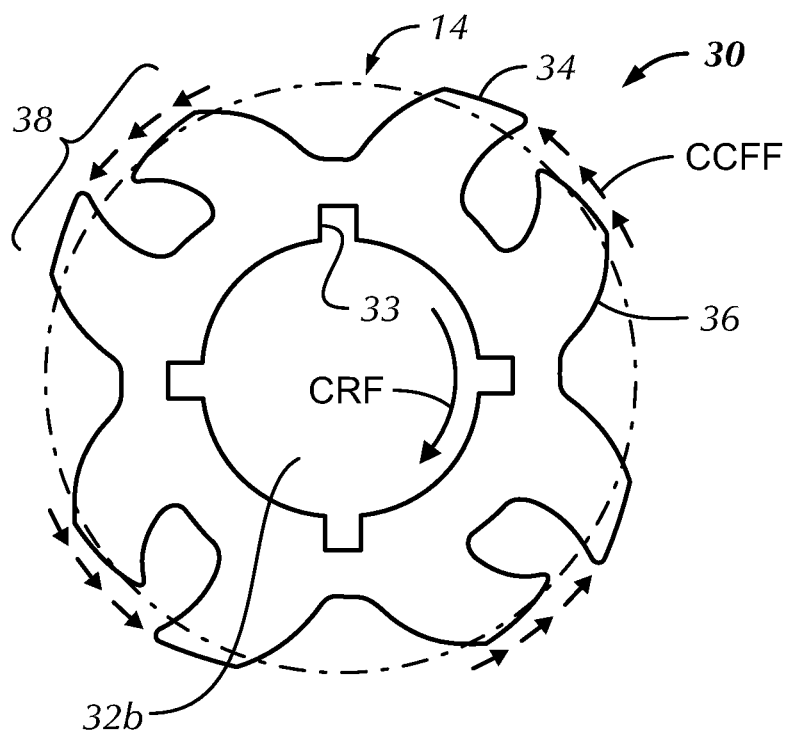
FIG. 7A is an enlarged, top plan view of the friction pad of FIG. 1 under the application of a clockwise rotational force thereto.

The cartridge 14 being rotationally fixed, e.g., within an injector, functions as an anchor point for the friction paid 30. As should be understood by those of ordinary skill in the art, therefore, clockwise rotational force CRF, i.e., clockwise torque, applied onto the friction pad 30 creates an opposite, counter-clockwise frictional force CCFF between the ends of the fingers 34, 36 and the sidewall of the rotationally fixed cartridge reservoir 14c. As shown in FIG. 7A, the direction of counter-clockwise frictional force CCFF is opposite to the clockwise direction of curvature of the first set of fingers 34. Accordingly, the counter-clockwise frictional force CCFF, acting to bend the first set of fingers 34 backwards, further wedges the first set of fingers 34 against the sidewall of the cartridge reservoir 14c, thereby effectively increasing the normal force applied by the first set of fingers 34 onto the cartridge reservoir 14c, which substantially prevents rotation of the friction pad 30 relative to the cartridge 14. Therefore, if the axially fixed first shaft 16 rotates in the clockwise direction (first direction), the first set of fingers 34 of the friction pad 30 substantially prevents the second shaft 18 from rotating in the clockwise direction with the first shaft 16, thereby resulting in axial/linear extension of the second shaft 18 to engage and drive the piston 12 forward through the cartridge 14.

As should be understood by those of ordinary skill in the art, the forward directed force of the axially extending second shaft 18 via rotation of the first shaft 16, in combination with the rotational resistance provided by the friction pad 30, is configured to overcome resistance of the piston 12 and the friction pad 30 to axial translation/motion. For example, the actuator employed may provide sufficient rotational force to the first shaft 16 to effect axial movement. Additionally, the pitch of the screw threads of the shafts of the driving assembly 10 may be sufficiently small such that a large rotation is associated with a small linear movement, resulting in a mechanical advantage to axial movement. As also should be understood, the counter-clockwise frictional force CCFF is in the same direction as the counter-clockwise direction of curvature of the second set of fingers 36. Accordingly, the counter-clockwise frictional force CCFF applies a force bending the fingers 36 away from the sidewall of the cartridge reservoir 14c (see FIG. 7A), thereby decreasing the normal force of the second set of fingers 36 on the cartridge reservoir 14c. Such decreased normal force assists in reducing the resistance of the friction pad 30 to axial translation.

Figure 7B:
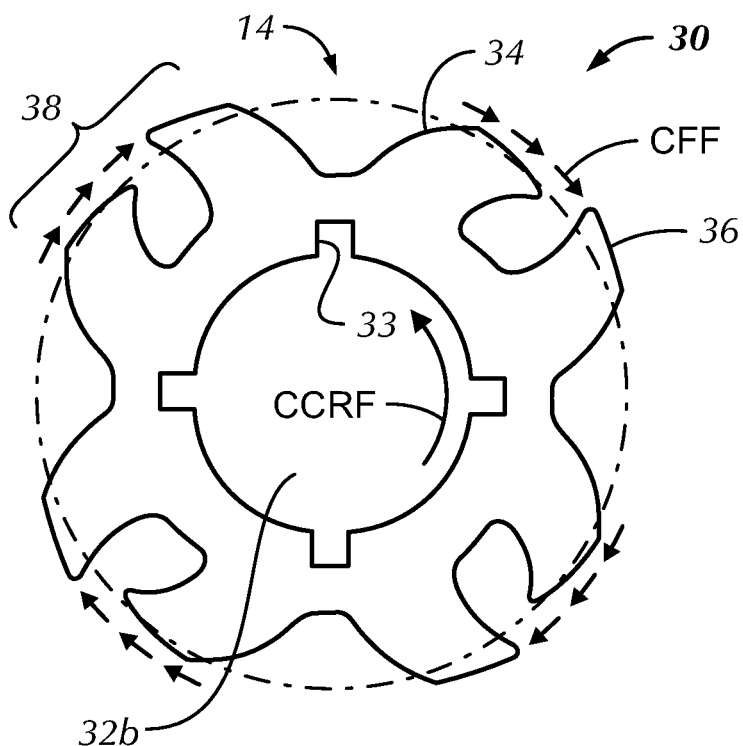
FIG. 7B is an enlarged, top plan view of the friction pad of FIG. 1 under the application of a counter-clockwise rotational force thereto.

Conversely, counter-clockwise rotational force CCRF, i.e., counter-clockwise torque, applied onto the friction pad 30 creates an opposite, clockwise frictional force CFF between the ends of the fingers 34, 36 and the sidewall of the rotationally fixed cartridge reservoir 14c. As shown in FIG. 7B, the direction of clockwise frictional force CFF is opposite to the counter-clockwise direction of curvature of the second set of fingers 36. Accordingly, the clockwise frictional force CFF, acting to bend the second set of fingers 36 backwards, further wedges the second set of fingers 36 against the sidewall of the cartridge reservoir 14c, thereby effectively increasing the normal force applied by the second set of fingers 36 onto the cartridge reservoir 14c, which substantially prevents rotation of the friction pad 30 relative to the cartridge 14. Therefore, if the axially fixed first shaft 16 rotates in the counter-clockwise direction (second direction), the second set of fingers 36 of the friction pad 30 substantially prevents the second shaft 18 from rotating in the counter-clockwise direction with the first shaft 16, thereby resulting in axial/linear extension of the second shaft 18 to engage and drive the piston 12 forward through the cartridge 14. The clockwise frictional force CFF, being in the same direction as the clockwise direction of curvature of the first set of fingers 34, applies a force bending the first set of fingers 34 away from the sidewall of the cartridge reservoir 14c, thereby decreasing the normal force of the first set of fingers 34 on the cartridge reservoir 14c and minimizing the resistance of the friction pad 30 to axial translation.

Advantageously, therefore, the friction pad 30 is configured to provide bi-directional rotational resistance to the second shaft 18 relative to a rotationally fixed cartridge 14. As should also be understood, the mechanical fixation between the friction pad 30 and the pushing cover 24 provides stronger rotational resistance therebetween than the rotational resistance provided by the friction pad 30 relative to the cartridge 14. Thus, rotational resistance provided by the friction pad 30 relative to the cartridge 14 is ensured to translate to the second shaft 18 (as the friction pad 30 and the pushing cover 24 will not rotate relative to one another). Therefore, irrespective of the direction of rotation of the axially fixed first shaft 16, the second shaft 18 is substantially prevented from rotating relative to the cartridge 14, thereby enabling linear extension of the driving assembly 10. Accordingly, the bi-directional rotational resistance provided by the friction pad 30 negates a required orientation of the friction pad 30 relative to the driving assembly 10, thereby simplifying assembly of the friction pad 30 to the driving assembly 10.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as set forth in the appended claims.

We claim:

1. An assembly for advancing a piston through a rotationally fixed cartridge, the cartridge having a front end, an open rear end and a substance filled therein between the piston and the front end, the assembly comprising:
    an axially fixed first member rotatable in either a first rotational direction or an opposing second rotational direction;
    an axially movable, rotatable second member connected to the first member via a threaded connection and connectable to the piston, wherein the first member comprises a first shaft and the second member comprises a second shaft; and
    a friction pad rotationally fixedly connected with a distal end of the second member, the friction pad comprising a central disk, a first set of fingers extending radially outwardly from the central disk and a second set of fingers extending radially outwardly from the central disk, wherein both the first set and the second set of fingers are configured to contact an interior side wall of the cartridge, the first set of fingers being angled toward the first rotational direction and configured to wedge the friction pad between the interior side wall and the second member upon rotation of the first member in the first rotational direction, thereby substantially preventing rotation of the friction pad and the second member in the first rotational direction relative to the cartridge, and the second set of fingers being angled toward the second rotational direction and configured to wedge the friction pad between the interior side wall and the second member upon rotation of the first member in the second rotational direction, thereby substantially preventing rotation of the friction pad and the second member in the second rotational direction relative to the cartridge.

2. The assembly of claim 1, wherein the fingers of the first and second sets are arcuate.

3. The assembly of claim 1, wherein each finger of the first set of fingers is positioned opposing a finger of the second set of fingers, thereby forming a respective pair of fingers.

4. The assembly of claim 3, wherein the fingers of each respective pair of fingers are positioned mirroring one another.

5. The assembly of claim 1, wherein each of the first and second sets of fingers includes four fingers.

6. The assembly of claim 1, wherein the fingers of the first set are substantially equally spaced apart about a periphery of the central disk, and wherein the fingers of the second set are substantially equally spaced apart about the periphery of the central disk.

7. The assembly of claim 1, wherein the central disk of the friction pad comprises an inner periphery defining a central aperture and a plurality of angularly spaced slots in the inner periphery.

8. The assembly of claim 7, further comprising a friction pad adapter connecting the friction pad with the second member, the friction pad being rotationally fixed to the second member and having a plurality of tabs corresponding to, and engaging, the plurality of slots in the friction pad for rotational fixation therewith.

9. The assembly of claim 8, wherein the friction pad is axially fixed with the friction pad adapter via the engagement between the slots and the corresponding tabs.

10. The assembly of claim 1, further comprising an axially movable and rotatable third shaft positioned between the first shaft and the second shaft, the third shaft being threadedly engaged with the first shaft and threadedly engaged with the second shaft.

* * * * *